(12) United States Patent
Suzuki

(10) Patent No.: US 7,142,630 B2
(45) Date of Patent: Nov. 28, 2006

(54) X-RAY COMPUTED TOMOGRAPHY APPARATUS WITH X-RAY INTENSITY CONTROL

(75) Inventor: Tetsuro Suzuki, Utsunomiya (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/107,901

(22) Filed: Apr. 18, 2005

(65) Prior Publication Data

US 2005/0185760 A1   Aug. 25, 2005

Related U.S. Application Data

(63) Continuation of application No. 10/262,895, filed on Oct. 3, 2002, now abandoned.

(30) Foreign Application Priority Data

| Oct. 22, 2001 | (JP) | ............................. 2001-324024 |
| Sep. 24, 2002 | (JP) | ............................. 2002-276917 |

(51) Int. Cl.
 *H05G 1/34* (2006.01)
(52) U.S. Cl. ........................ 378/16; 378/108; 378/109; 378/110
(58) Field of Classification Search .................. 378/16, 378/108, 109, 110, 111, 112, 113
See application file for complete search history.

(56) References Cited

U.S. PATENT DOCUMENTS

| 5,103,469 | A | 4/1992 | Tanaka ........................ 378/16 |
| 5,379,333 | A | 1/1995 | Toth ............................. 378/16 |
| 5,400,378 | A | 3/1995 | Toth ............................. 378/16 |
| 5,450,462 | A | 9/1995 | Toth et al. .................... 378/16 |
| 5,485,494 | A | 1/1996 | Williams et al. ............... 378/16 |
| 5,625,662 | A | 4/1997 | Toth et al. .................... 378/16 |
| 5,696,807 | A | 12/1997 | Hsieh ......................... 378/109 |
| 5,822,393 | A | 10/1998 | Popescu ..................... 378/108 |
| 5,867,555 | A | 2/1999 | Popescu et al. ............... 378/16 |
| 5,982,846 | A * | 11/1999 | Toth et al. .................... 378/19 |
| 6,061,420 | A | 5/2000 | Strong et al. ................. 378/4 |
| 6,067,341 | A | 5/2000 | Horiuchi ...................... 378/8 |
| 6,094,468 | A | 7/2000 | Wilting et al. ................ 378/8 |
| 6,173,033 | B1 | 1/2001 | Klingenbeck-Regn et al. ........................... 378/20 |
| 6,198,789 | B1 | 3/2001 | Dafni ............................. 378/8 |
| 6,385,280 | B1 | 5/2002 | Bittl et al. .................... 378/16 |
| 6,490,337 | B1 | 12/2002 | Nagaoka et al. .............. 378/20 |
| 6,754,301 | B1 * | 6/2004 | Horiuchi ...................... 378/16 |
| 6,795,526 | B1 * | 9/2004 | Kump et al. ................. 378/116 |

FOREIGN PATENT DOCUMENTS

| JP | 2605048 | 4/2000 |
| JP | 2000-262512 | 9/2000 |
| WO | WO 98/33361 | 7/1998 |

* cited by examiner

*Primary Examiner*—Allen C. Ho
(74) *Attorney, Agent, or Firm*—Oblon, Spivak, McClelland, Maier & Neustadt, P.C.

(57) ABSTRACT

An X-ray computed tomography apparatus includes an X-ray tube, a high voltage generator which generates a high voltage to be applied to the X-ray tube, an X-ray detector having a plurality of X-ray detection element lines, a scanogram generating unit which generates a scanogram on the basis of an output from the X-ray detector, a reconstructing unit which reconstructs an image on the basis of an output from the X-ray detector, a tube current determining unit which determines a tube current value on the basis of the pixel values of a plurality of pixels included in a two-dimensional partial region of the scanogram, and a control unit which controls the high voltage generator on the basis of the determined tube current value.

25 Claims, 18 Drawing Sheets

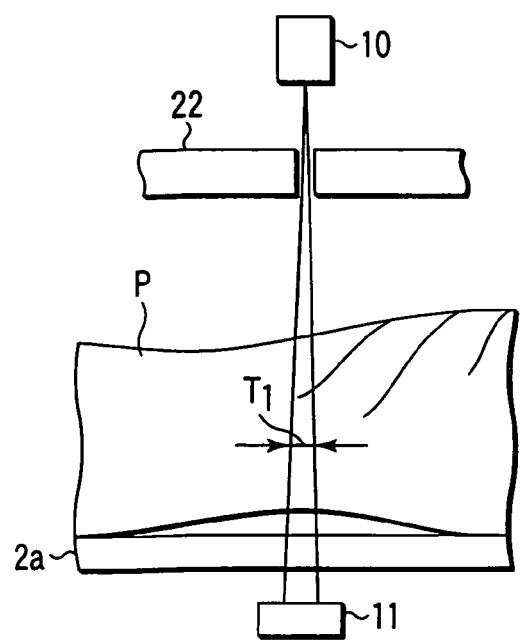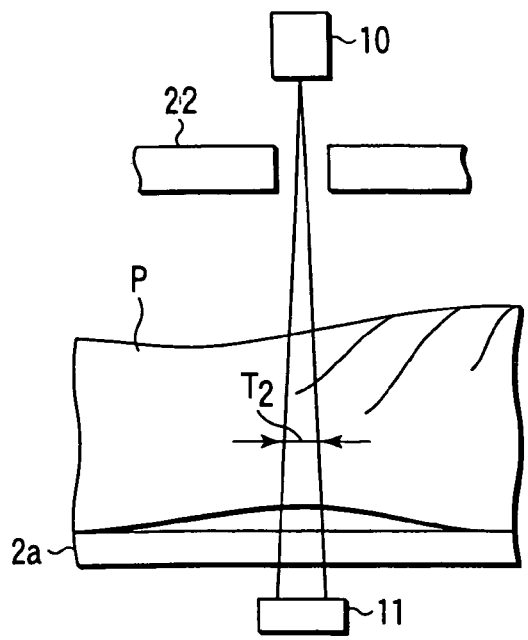
FIG. 1A PRIOR ART — SCANOGRAM DATA ACQUISITION
FIG. 1B PRIOR ART — SCANNING
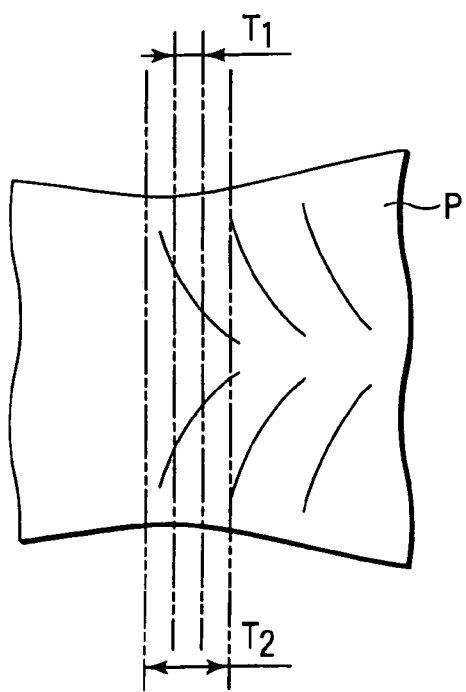
FIG. 1C PRIOR ART

SCANOGRAM DATA ACQUISITION

SCANNING

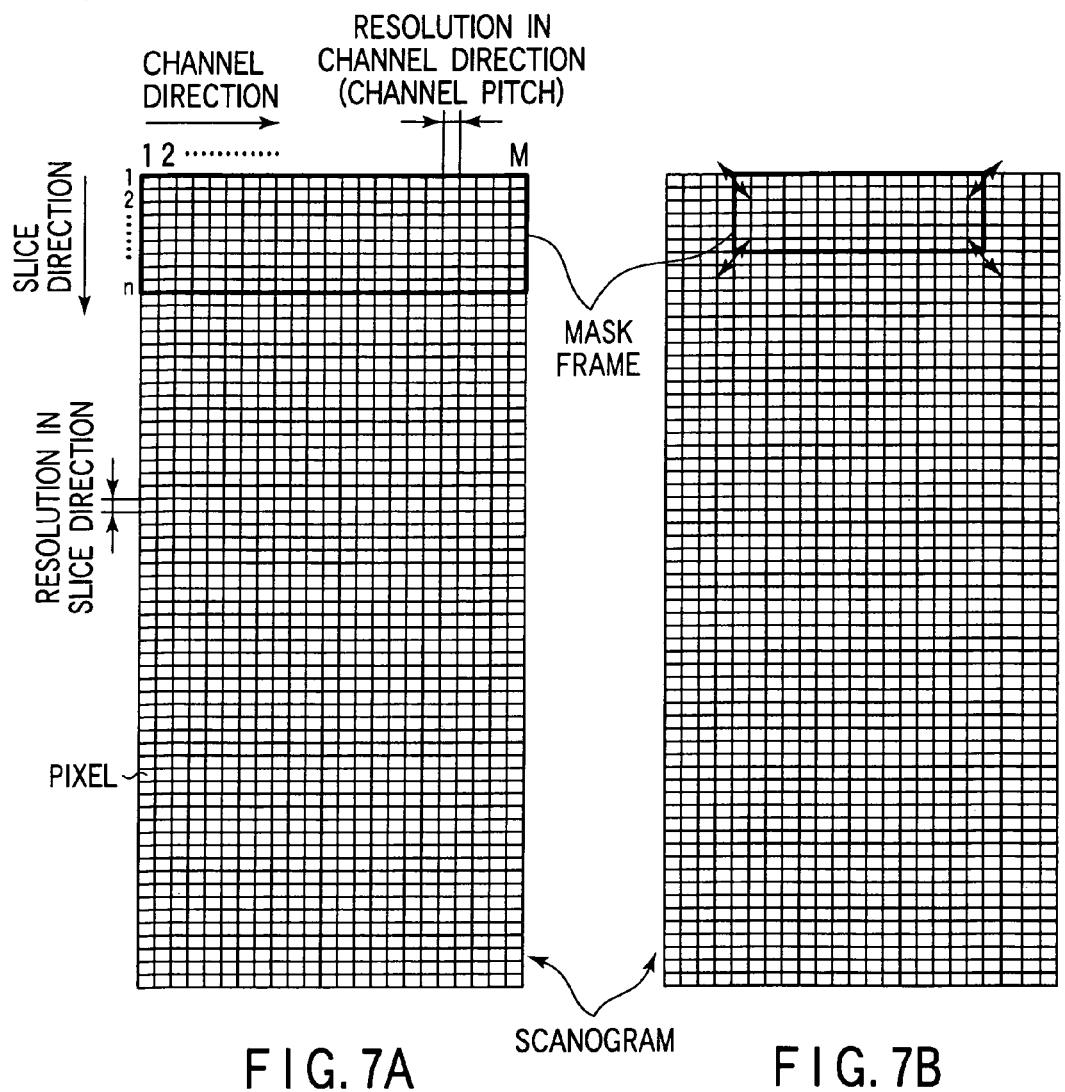
FIG. 7A   FIG. 7B   SCANOGRAM

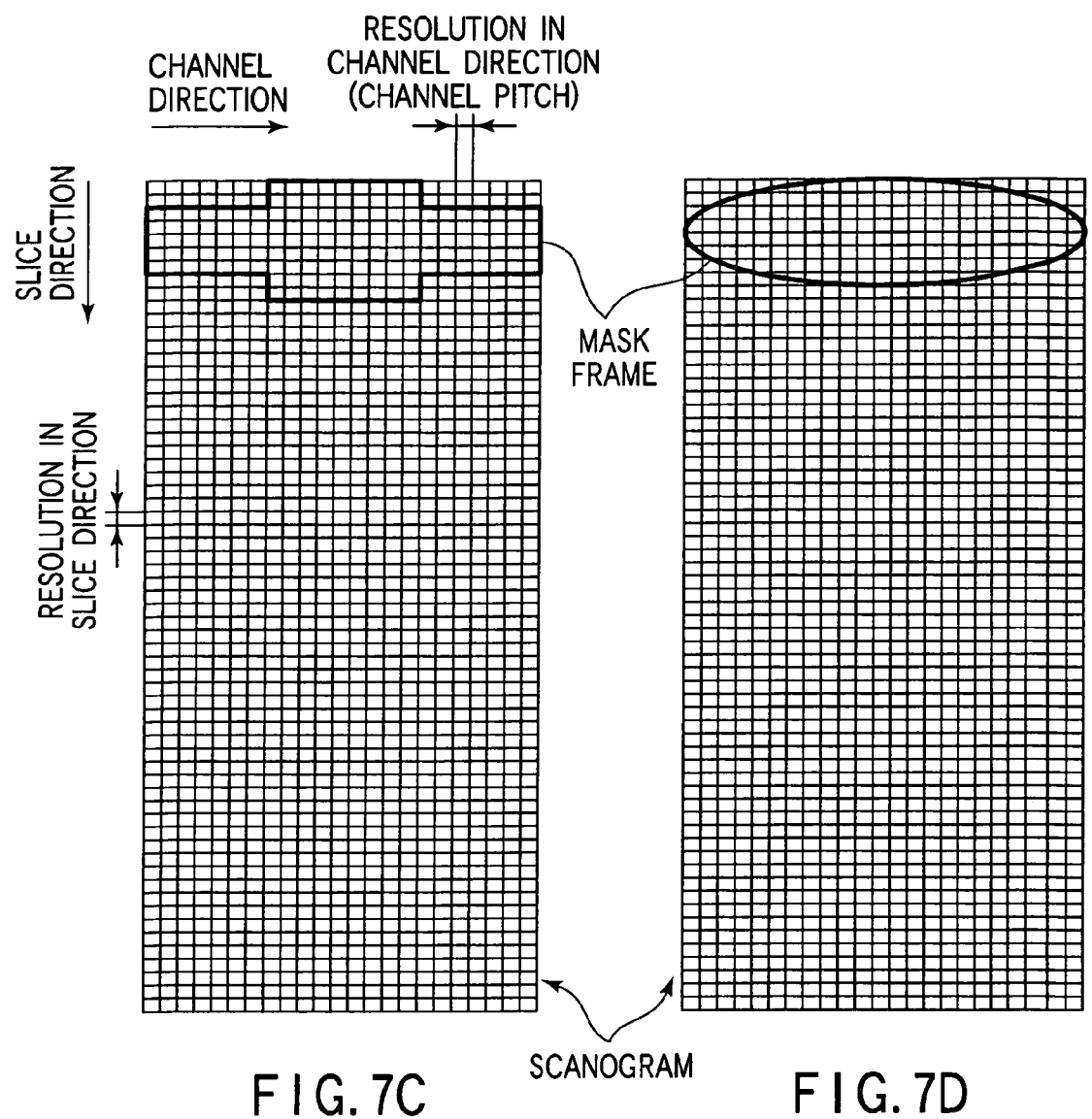

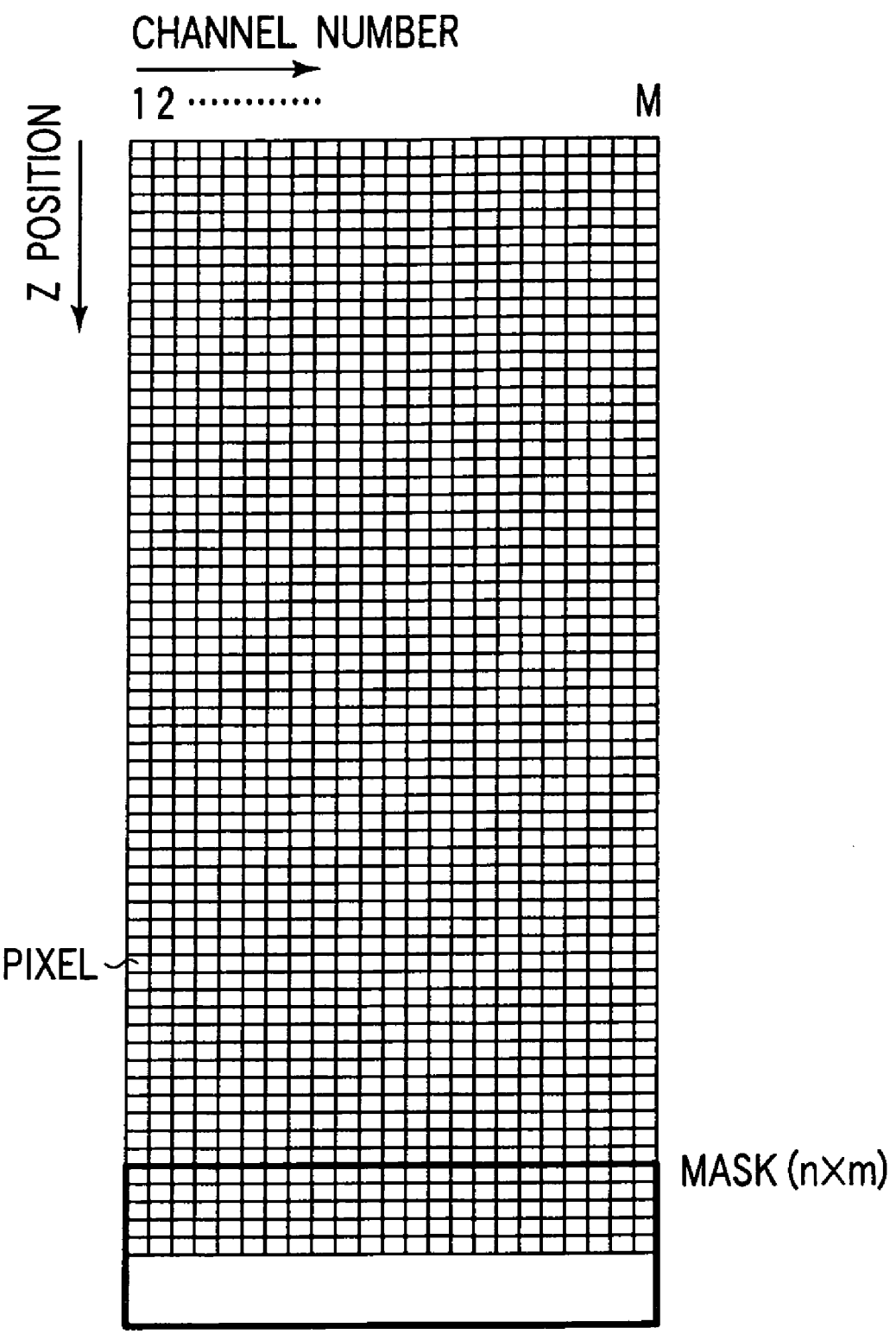
F I G. 9C

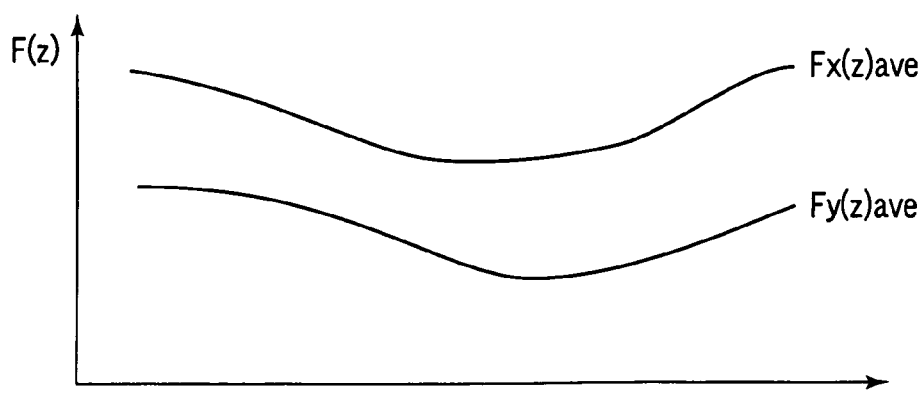
F I G. 15A
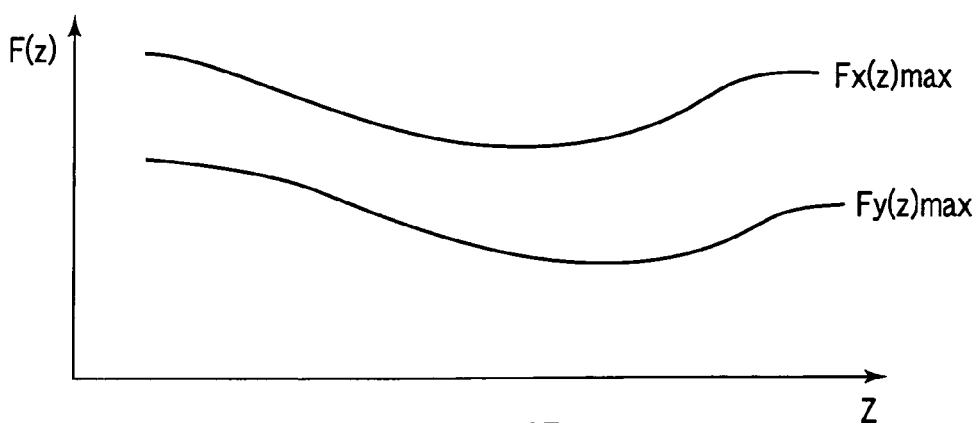
F I G. 15B
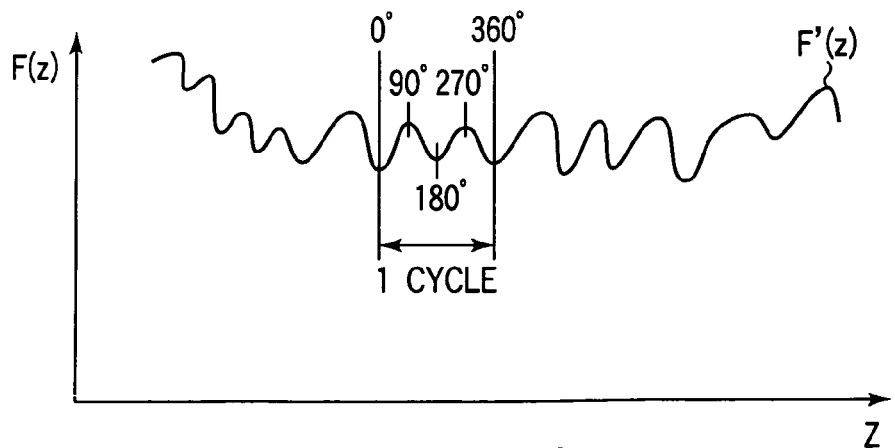
F I G. 15C

BEFORE ONE ROTATION

AFTER ONE ROTATION

X-RAY COMPUTED TOMOGRAPHY APPARATUS WITH X-RAY INTENSITY CONTROL

CROSS-REFERENCE TO RELATED APPLICATIONS

This application is a continuation application of, and claims priority to, application Ser. No. 10/262,895, filed Oct. 3, 2002, which is based upon and claims the benefit of priority from the prior Japanese Patent Applications No. 2001-324024, filed Oct. 22, 2001; No. 2002-276917, filed Sep. 24, 2002, the entire contents of the above applications are incorporated herein by reference.

BACKGROUND OF THE INVENTION

1. Field of the Invention

The present invention relates to an X-ray computed tomography apparatus including an X-ray tube and multi-slice X-ray detectors.

2. Description of the Related Art

A significant challenge for recent X-ray computed tomographic imaging apparatuses is to realize both an improvement in image quality and a decrease in dosage. Image quality improves as the intensity of X-rays with which an object to be examined is irradiated decreases, and vice versa.

In a conventional apparatus, the intensity of X-ray generated during a helical scan is maintained at a constant value. Recently, however, techniques of changing the intensity of X-rays in-accordance with the X-ray transmission factor which changes in accordance with a region of the object have been proposed. In many of these proposals, the X-ray intensity is changed in accordance with a value at a given point on a scanogram. As is known, a scanogram is the two-dimensional intensity distribution of transmitted X-rays which is acquired for a scan-plan.

To acquire scanogram data, an X-ray tube 10 is fixed at a given rotational angle, as shown in FIGS. 1A and 2A. A table top 2a is moved at a constant velocity. During this period, signals are repeatedly read from an X-ray detector 11 at a predetermined cycle.

This X-ray intensity control is effective in a single-slice scan shown in FIG. 1B. As shown in FIG. 2B, however, X-ray intensity cannot be satisfactorily optimized for a multi-slice scan (also called a volume scan). The biggest reason for this is that in a multi-slice scan, data are acquired at once in a wide range with a slice width T2 larger than a slice width T1 in scanogram data acquisition.

BRIEF SUMMARY OF THE INVENTION

It is an object of the present invention to further optimize X-ray intensity in a multi-slice scan.

According to the first aspect of the present invention, there is provided an X-ray computed tomography apparatus comprising an X-ray tube which generates X-rays with which an object to be examined is irradiated, a high voltage generator which generates a high voltage to be applied to the X-ray tube, an X-ray detector which has a plurality of X-ray detection element lines for detecting X-rays transmitted through the object, a scanogram generating unit which generate a scanogram on the basis of an output from the X-ray detector, a reconstructing unit which reconstructs an image on the basis of the output from the X-ray detector, a tube current determining unit which determines a tube current value for the X-ray tube on the basis of pixel values of a plurality of pixels included in a two-dimensional partial region of the scanogram, and a control unit which controls the high voltage generator on the basis of the determined tube current value.

According to the second aspect of the present invention, there is provided an X-ray computed tomography apparatus comprising an X-ray tube which generates X-rays with which an object to be examined is irradiated, a high voltage generator which generates a high voltage to be applied to the X-ray tube, an X-ray detector which has a plurality of X-ray detection element lines for detecting X-rays transmitted through the object, a reconstructing unit which reconstructs an image on the basis of outputs from at least two X-ray detection element lines selected in accordance with a slice thickness and the number of slices indicated by a user instruction, a tube current determining unit which determines a tube current value for the X-ray tube on the basis of an output distribution, X-ray transmission factor distribution, or X-ray attenuation factor distribution of the X-ray detector which corresponds to a range corresponding to the slice thickness and the number of slices, and a control unit which controls the high voltage generator on the basis of the determined tube current value.

According to the third aspect of the present invention, there is provided an X-ray computed tomography apparatus comprising an X-ray tube which generates X-rays with which an object to be examined is irradiated, a high voltage generator which generates a high voltage to be applied to the X-ray tube, an X-ray detector which has a plurality of X-ray detection element lines for detecting X-rays transmitted through the object, a reconstructing unit which reconstructs an image on the basis of the output from the X-ray detector, and a control unit which dynamically controls the high voltage generator on the basis of a profile of the object in a slice direction which is associated with an X-ray transmission factor or a similar index.

According to the fourth aspect of the present invention, there is provided an X-ray computed tomography apparatus comprising an X-ray tube which generates X-rays with which an object to be examined is irradiated, a high voltage generator which generates a high voltage to be applied to the X-ray tube, an X-ray detector which has a plurality of X-ray detection element lines for detecting X-rays transmitted through the object, a moving mechanism which moves the object relative to the X-ray tube and the X-ray detector, a reconstructing unit which reconstructs an image on the basis of outputs from at least two detection element lines selected from the plurality of X-ray detection element lines in accordance with a user instruction, and a control unit which dynamically controls a tube current value for the X-ray tube along with relative movement of the object on the basis of outputs from at least two X-ray detection element lines preceding at least the two selected detection element lines.

According to the fifth aspect of the present invention, there is provided an X-ray computed tomography apparatus comprising an X-ray tube which generates X-rays with which an object to be examined is irradiated, a high voltage generator which generates a high voltage to be applied to the X-ray tube, an X-ray detector which has a plurality of X-ray detection element lines for detecting X-rays transmitted through the object, a moving mechanism which moves the object relative to the X-ray tube and the X-ray detector, a reconstructing unit which reconstructs an image on the basis of outputs from at least two detection element lines selected from the plurality of X-ray detection element lines in accordance with a user instruction, and a control unit which dynamically controls a tube current value for the X-ray tube along with relative movement of the object on the basis of outputs from the at least two selected X-ray detection element lines.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constituted a part of the specification, illustrate presently preferred embodiments of the invention, and together with the general description given above and the detailed description of the preferred embodiments given below, serve to explain the principles of the invention.

FIGS. 1A to 1C are views showing a conventional single-slice scan;

FIGS. 7A to 7D are views showing an example of the mask setting window in step S2 of FIG. 5;

FIGS. 9A to 9C are views showing the start position, intermediate position, and end position of a mask in step S3 of FIG. 5;

FIGS. 15A to 15C are graphs showing a change in tube current over time in the modification to this embodiment;

DETAILED DESCRIPTION OF THE INVENTION

An X-ray computed tomographic imaging apparatus (X-ray CT apparatus) according to an embodiment of the present invention will be described below with reference to the views of the accompanying drawing. Note that X-ray CT apparatuses include various types of apparatuses, e.g., a rotate/rotate type apparatus in which an X-ray tube and X-ray detector rotate together around an object to be examined, and a stationary/rotate type apparatus in which many detection elements are arrayed in the form of a ring, and only an X-ray tube rotates around an object to be examined. The present invention can be applied to either type. In this case, the rotate/rotate type, which is currently the mainstream, will be exemplified.

In order to reconstruct one-slice tomographic image data, 360° projection data corresponding to one rotation around an object to be examined is required, or (180°+view angle) projection data is required in the half scan method. The present invention can be applied to either of these reconstruction schemes. The half scan method will be exemplified here.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified.

Recently, with advances toward the commercialization of a so-called multi-tube type X-ray CT apparatus having a plurality of pairs of X-ray tubes and X-ray detectors-mounted on a rotating ring, related techniques have been developed. The present invention can be applied to both a conventional single-tube type X-ray CT apparatus and a multi-tube type X-ray CT apparatus. The single-tube type X-ray CT apparatus will be exemplified here.

Figure 2A:
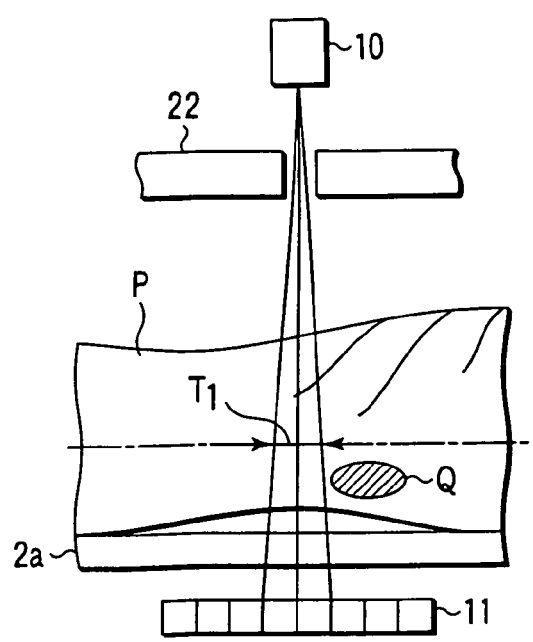
FIGS. 2A to 2C are views showing a conventional multi-slice scan.
Figure 2B:
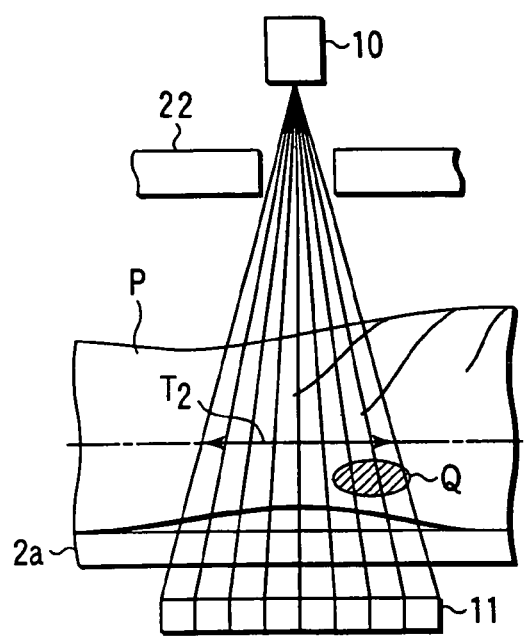
Figure 2C:
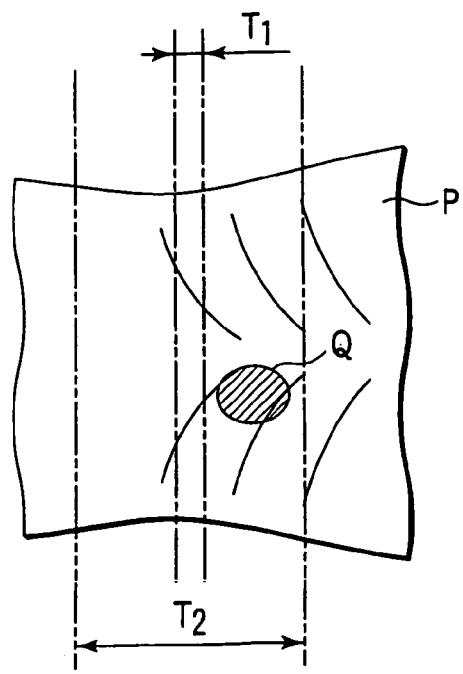
Figure 3:
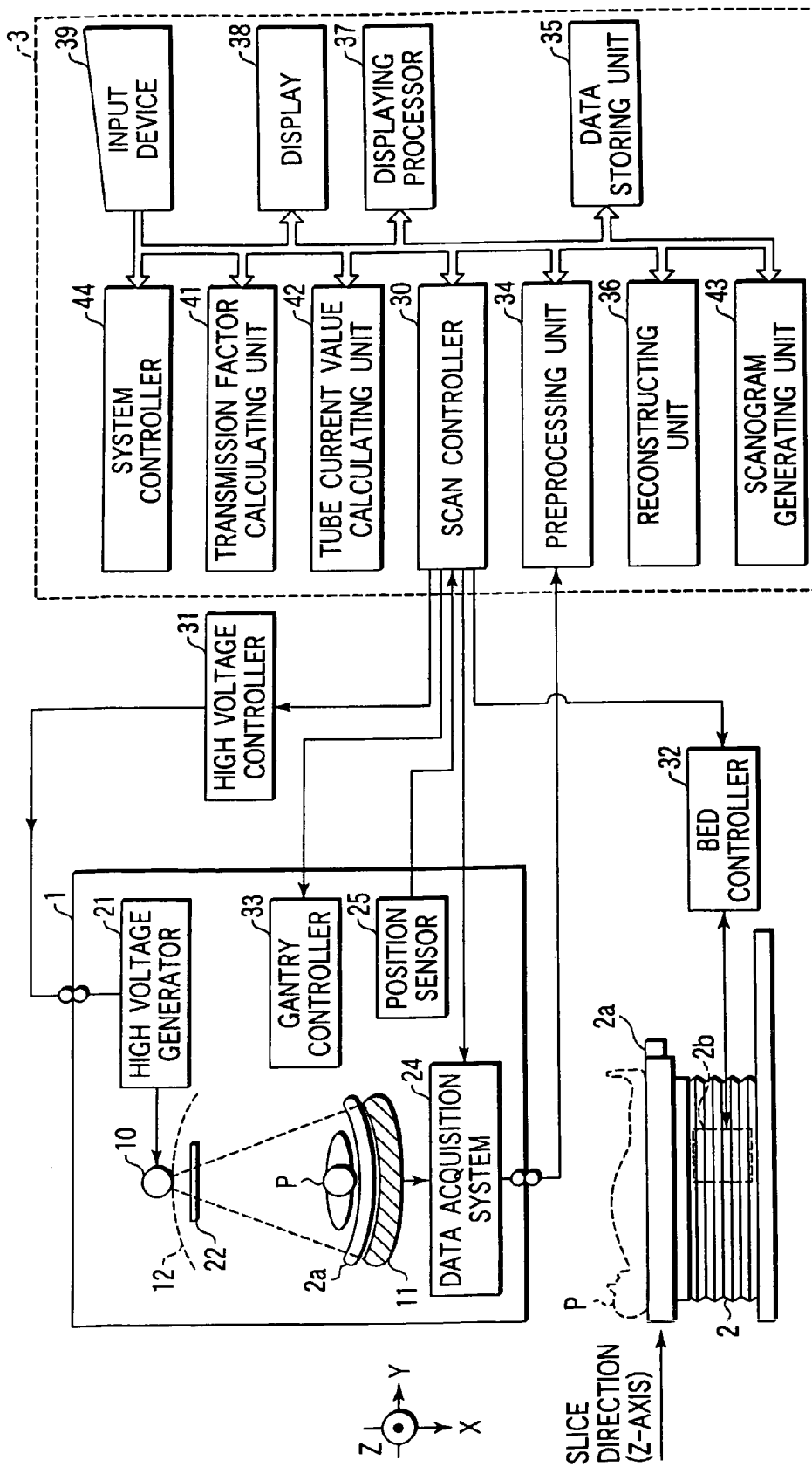
FIG. 3 is a block diagram showing the arrangement of an X-ray computed tomography apparatus according to an embodiment of the present invention.

FIG. 3 shows the arrangement of an X-ray computed tomographic imaging apparatus according to this embodiment. A substantially cylindrical rotating frame 12 is housed in a gantry 1. The rotating frame 12 is rotated by a gantry driving unit under the control of a gantry controller 33 in scan operation, and fixed at a predetermined angle position, e.g., an angle position of 0° by the braking function of the gantry driving unit at the time of scanogram data acquisition. An X-ray tube 10 and X-ray detector 11 are mounted on the rotating frame 12. A high voltage generator 21 applies a high voltage (tube voltage) between the cathode and the anode of the X-ray tube 10 under the control of a high voltage controller 31. The high voltage generator 21 supplies a filament current to the cathode filament under the control of the high voltage controller 31. A tube current that flows between the cathode and the anode is determined in accordance with the filament current. The intensity of X-rays generated is determined in accordance with the tube current.

Figure 4:
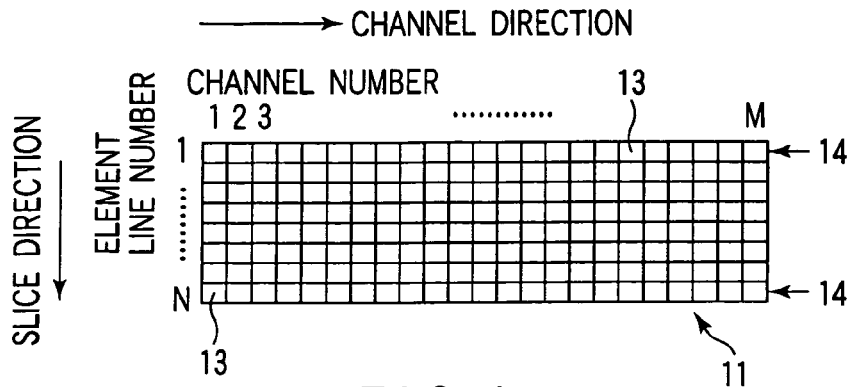
FIG. 4 is a plan view of an X-ray detector in FIG. 3.

A collimator 22 which trims X-rays into a pyramidal shape is attached to the X-ray radiation window of the X-ray tube 10. The opening degree of the collimator 22 is variable. The X-ray detector 11 opposes the X-ray tube 10 through an object P to be examined which is placed on a table top 2a of a bed 2. As shown in FIG. 4, the X-ray detector 11 has a plurality of X-ray detection element lines 14, N X-ray detection element lines 14 in this case, arranged along the slice direction. Each X-ray detection element line 14 has a plurality of X-ray detection elements 13, M X-ray detection elements 13 in this case, arranged in the channel direction. The table top 2a of the bed 2 is moved along the slice direction by a bed driving unit 2b such as a servo motor under the control of a bed controller 32.

A cabinet 3 includes a system controller 44 for controlling the operation of the overall system, a scan controller 30, a preprocessing unit 34, a data storing unit 35, a reconstructing unit 36, a display processor 37, a display 38, an input device (console) 39, a scanogram generating unit 43, a transmission factor calculating unit 41, and a tube current value calculating unit 42.

Figure 6A:
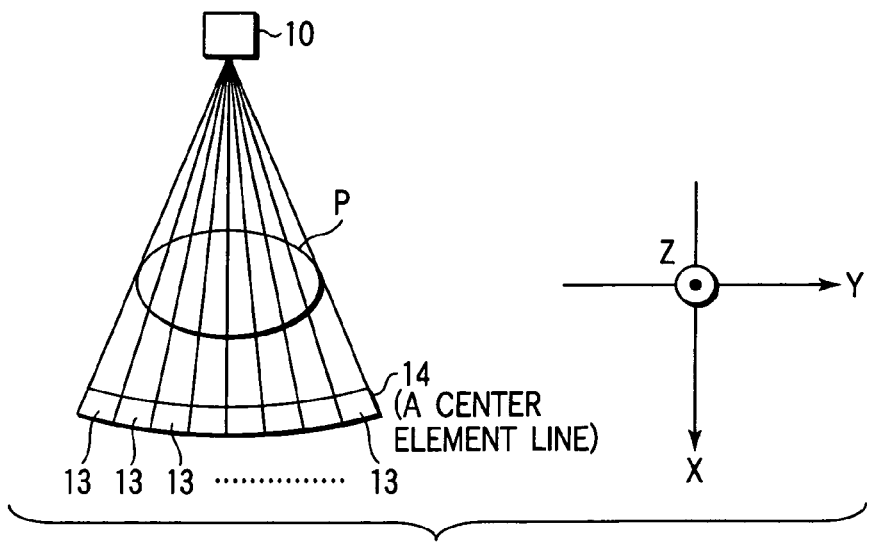
FIGS. 6A and 6B are views showing a data profile acquired by a center element line of an X-ray detector in FIG. 2.
Figure 6B:
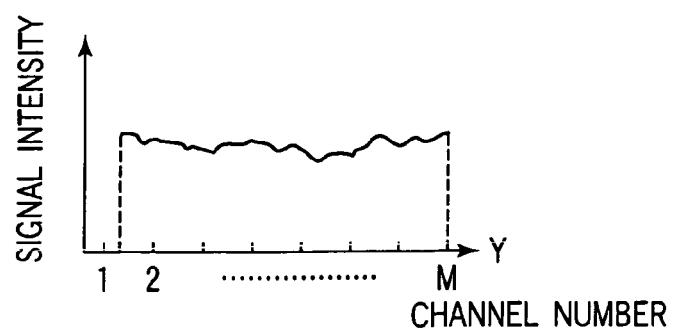
Figure 5:
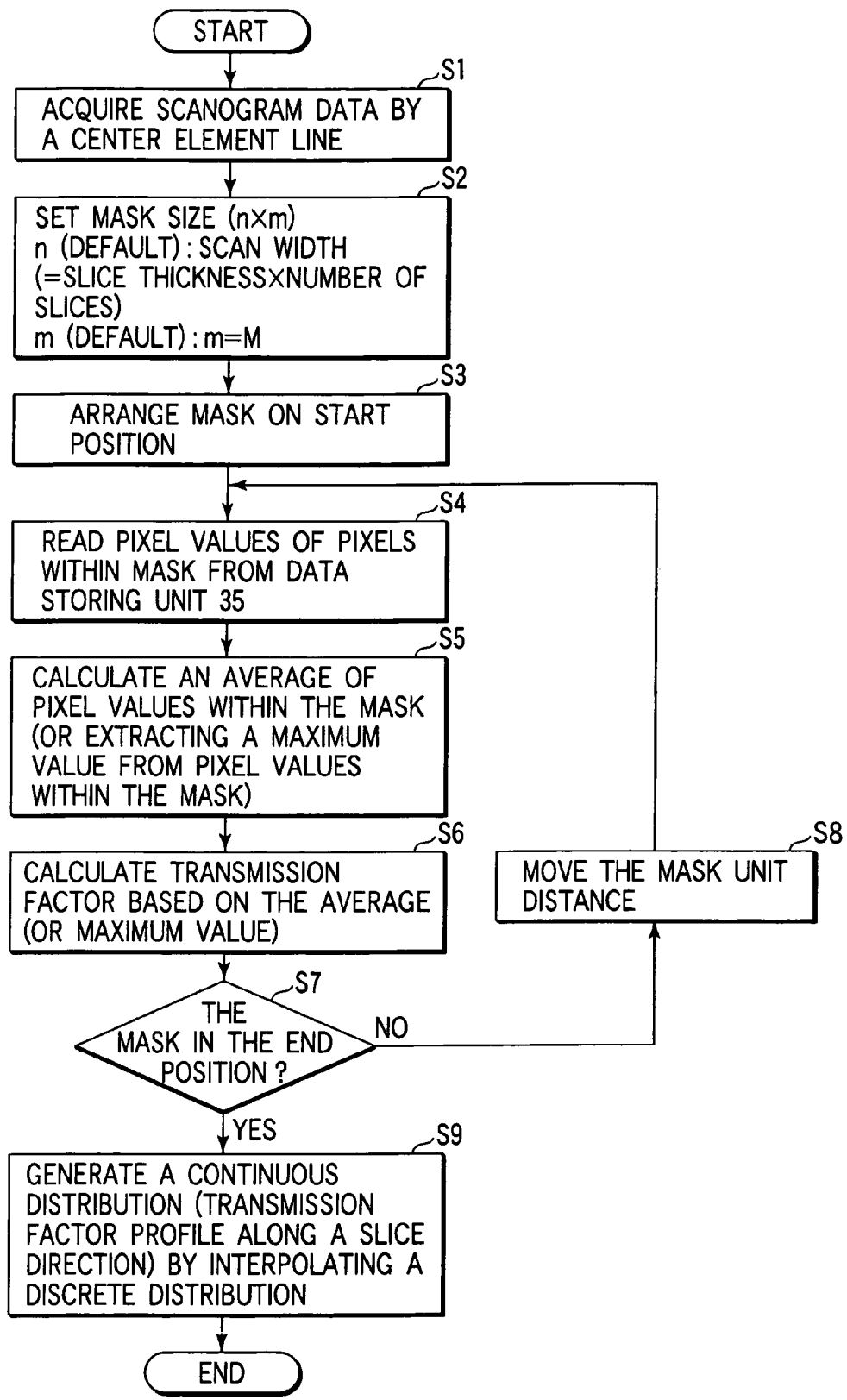
FIG. 5 is a flow chart showing the flow of transmission factor calculation processing by a transmission factor calculating unit in FIG. 3.

FIG. 5 shows a transmission factor calculation procedure executed by the transmission factor calculating unit 41. First of all, scanogram data are acquired (S1). Scanogram data is essentially data that is acquired to be referred to when a scan plan including a scan range, imaging conditions, and the like is made. This scanogram data is also used as basic data for the calculation of a transmission factor. As shown in FIG. 6A, scanogram data is generally acquired by the center element line 14. In order to acquire scanogram data, the rotating frame 12 is fixed to, for example, an angle position of 0°, and the table top 2a is moved at a constant velocity. While the table top 2a is moved at a constant velocity, the X-ray tube 10 continuously emits X-rays having a low intensity. While X-rays are continuously emitted, signals are read from the center element line 14 at a predetermined cycle (see FIG. 6B). The resolution in the slice direction of a scanogram is determined by the cycle at which signals are read out and the moving velocity of the table top 2a. The resolution in the channel direction of a scanogram is defined by a channel pitch. Assuming that one channel corresponds to one element, the channel pitch is equal to the element pitch, i.e., the distance between the center points of adjacent detection elements.

The signals read at the predetermined cycle are sent to the scanogram generating unit 43 through a data acquisition system 24 and the preprocessing unit 34. The scanogram generating unit 43 associates channel number data and the position data in the slice direction of the table top 2a which is detected by a position sensor 25 with each channel data, thus generating scanogram data. The generated scanogram data is stored in the data storing unit 35.

Each pixel value of this scanogram represents the intensity of transmitted X-rays. An X-ray transmission factor at each position in the slice direction can be calculated from the intensity of transmitted X-rays and a know generated X-ray intensity. A transmission factor at each position is calculated from the pixel values of a plurality of pixels included in a two-dimensional area centered on the position. This two-dimensional area is called a mask.

The transmission factor calculating unit 41 sets a mask size (n×m) in accordance with a user instruction associated with the mask size input through the input device 39 (S2). To support inputting of a mask size, the display processor 37 displays a scanogram on the display 38 in accordance with the scanogram data read out from the data storing unit 35, and superimposes a mask frame on this scanogram.

Figure 8:
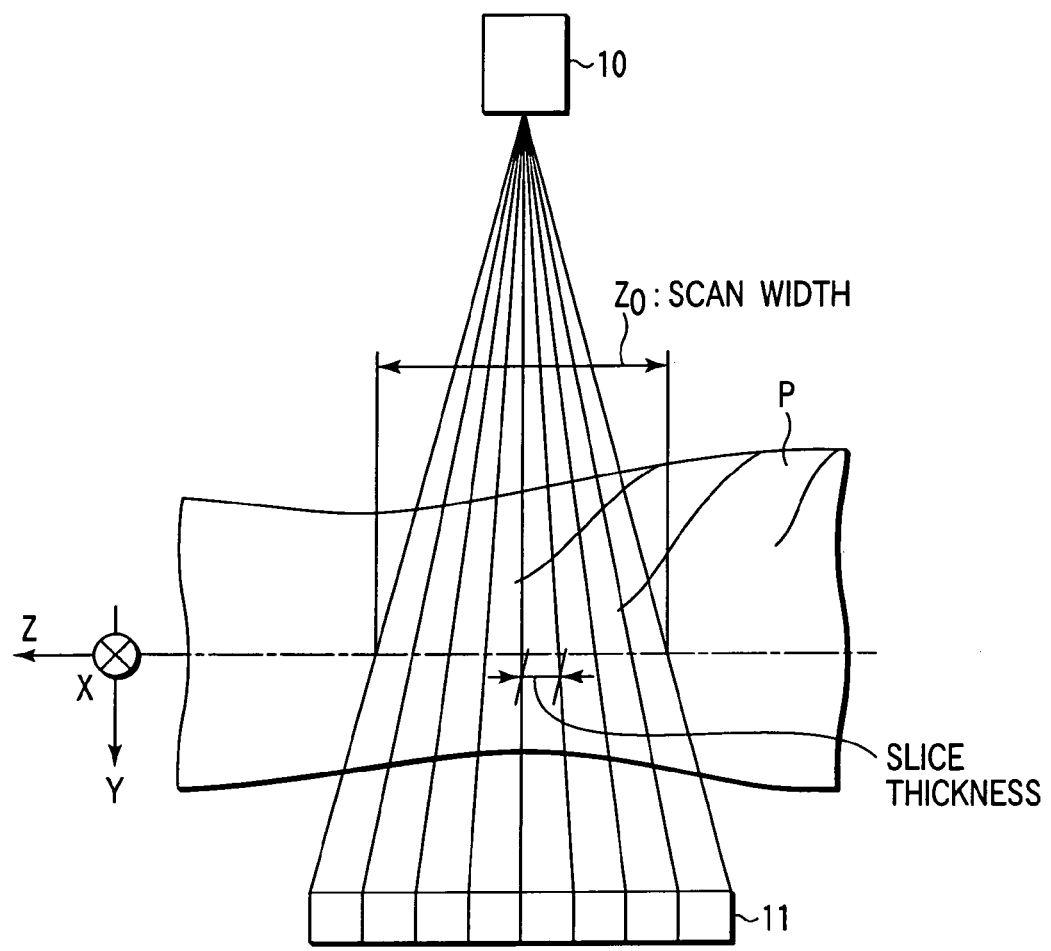
FIG. 8 is a view for a supplementary explanation of a scan width in step S2 of FIG. 5.

FIG. 7A shows an example of the scanogram and default mask frame displayed on the display 38. The default mask frame has a rectangular shape, and its matrix size is set to the number of pixels in the vertical direction, which is determined by the scan width divided by the resolution in the slice direction (=N) and the number of pixels in the horizontal direction, which is equal to the number of channels (=M) of each of the X-ray detection element lines 14. As shown in FIG. 8, the scan width is defined by the product of the number of slices and the slice thickness. The number of slices and the slice thickness are set by the user at the time of scan planning. The number of slices is set to at least two in a multi-slice scan. The slice thickness is defined by the thickness of one slice on the rotational center axis and selectively designated from a positive integer multiple of a reduced length on the rotational center axis of the sensible width of one X-ray detection element line 14.

As shown in FIG. 7B, the mask frame can be arbitrarily enlarged/reduced with the range of 2<n<N and 2<m<M in accordance with the operation of the input device 39 by the user. That is, a mask frame includes at least 2×2 pixels. In addition, as shown in FIG. 7C, the shape of the mask frame can be changed into an arbitrary polygonal shape including a cross shape in accordance with the operation of the input device 39 by the user. In addition, as shown in FIG. 7D, the shape of the mask frame can be changed into an elliptic or circular shape in accordance with the operation of the input device 39 by the user.

Figure 9A:
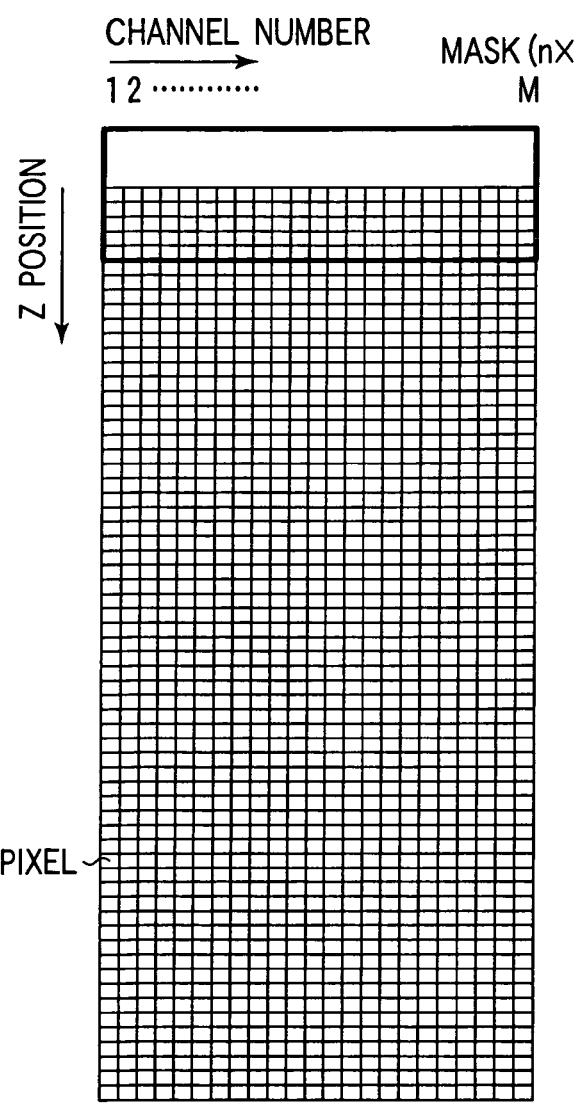

After a mask size is determined, the transmission factor calculating unit 41 places a mask at the start position with respect to the scanogram, as shown in FIG. 9A (S3). The pixel values of a plurality of pixels included in the mask at the position are selectively read out from the data storing unit 35 (S4). The average of the readout pixel values of the pixels is calculated (S5). The maximum value (or minimum value) of the readout pixel values of the pixels may be extracted instead of the average value. The user determines whether to calculate an average or extract a maximum or minimum value. If an average is selected, stable tube current control can be realized. If a maximum value is selected, tube current control effective for a reduction in dosage. If a minimum value is selected, tube current control effective for an increase in S/N can be realized.

Note that the average within this mask is equivalent to the value obtained by averaging the pixel values of a scanogram in the channel direction and calculating the moving average in the slice direction from the average in the channel direction.

The transmission factor calculating unit 41 then calculates a transmission factor F(z) corresponding to a center position z in the slice direction of the mask on the basis of the average (or maximum or minimum value) in the two-dimensional area according to the following equation (S6):

$$F(z) = \log(I_0/(I_0 - I_1))$$

where $I_0$ is the intensity of generated X-rays, and $I_1$ is the intensity of transmitted X-rays.

According to the above description, a tube current value is determined on the basis of scanogram data in a two-dimensional area. However, a tube current value may be determined on the basis of a distribution in a two-dimensional area associated with an output (called raw data) from the detector 11 before the creation of scanogram data. Raw data, scanogram data, and various types of index data obtained from the raw data are generically called X-ray data.

Figure 9B:
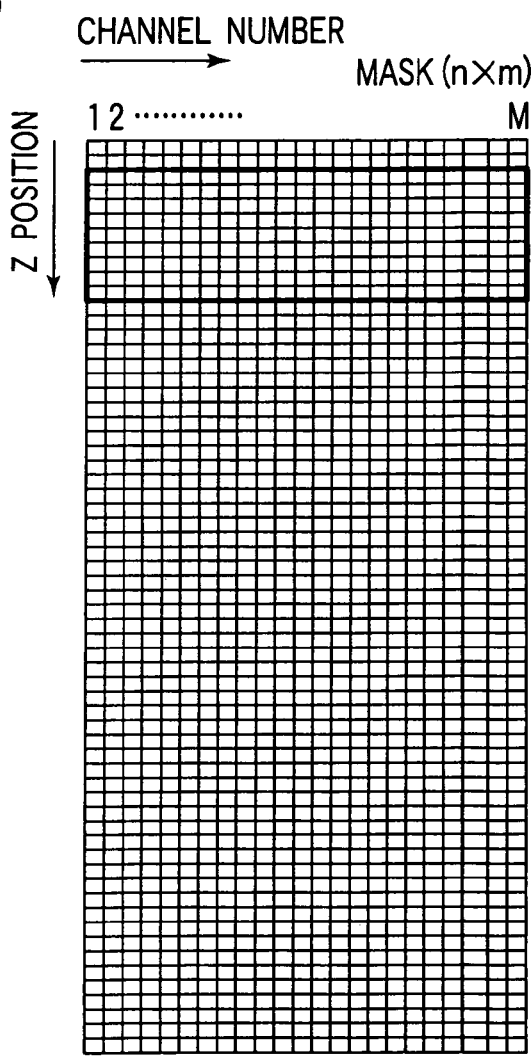
Figure 10A:
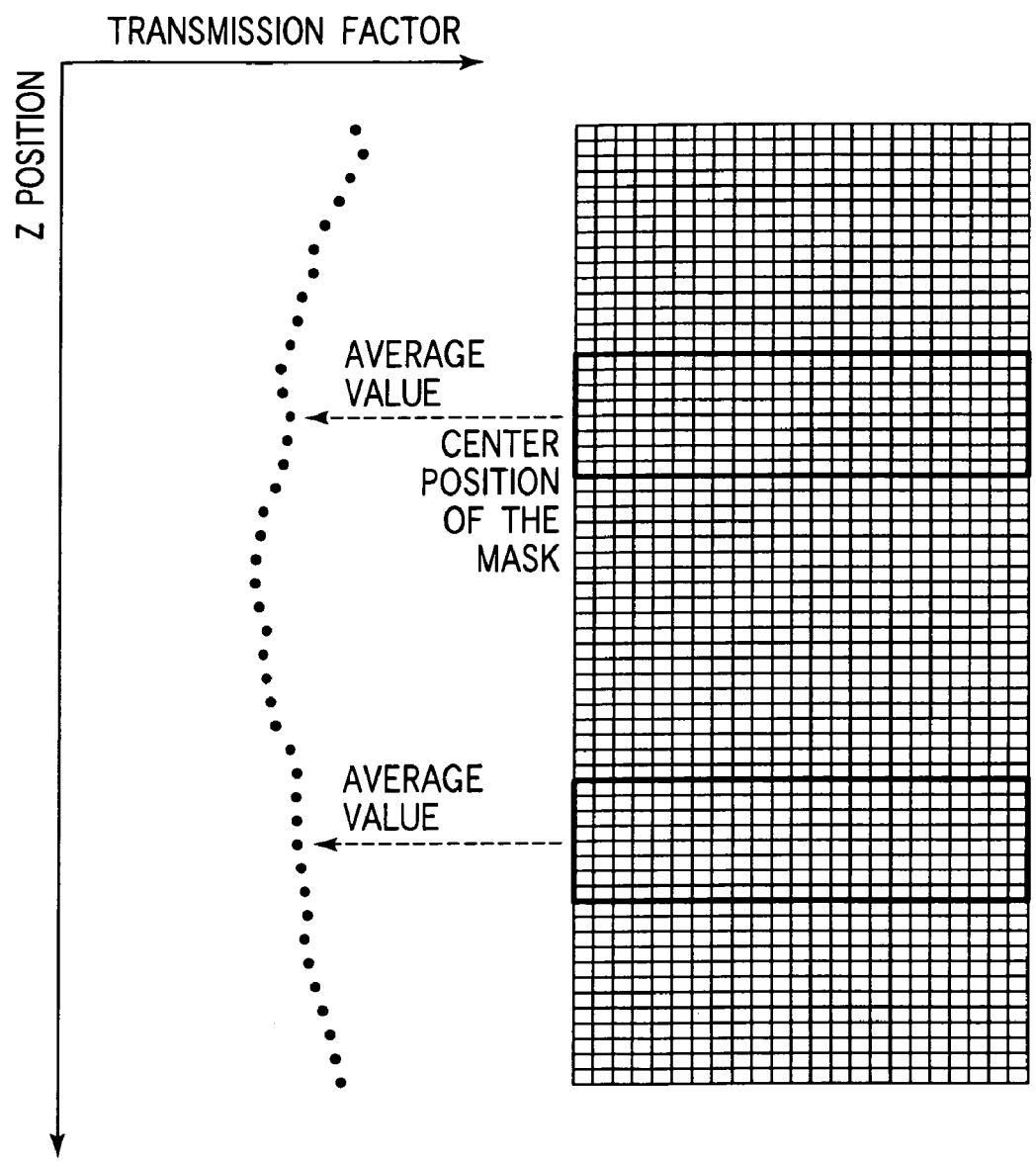
FIGS. 10A and 10B are views showing the discrete distribution of transmission factors calculated by the transmission factor calculating unit in FIG. 3.
Figure 10B:
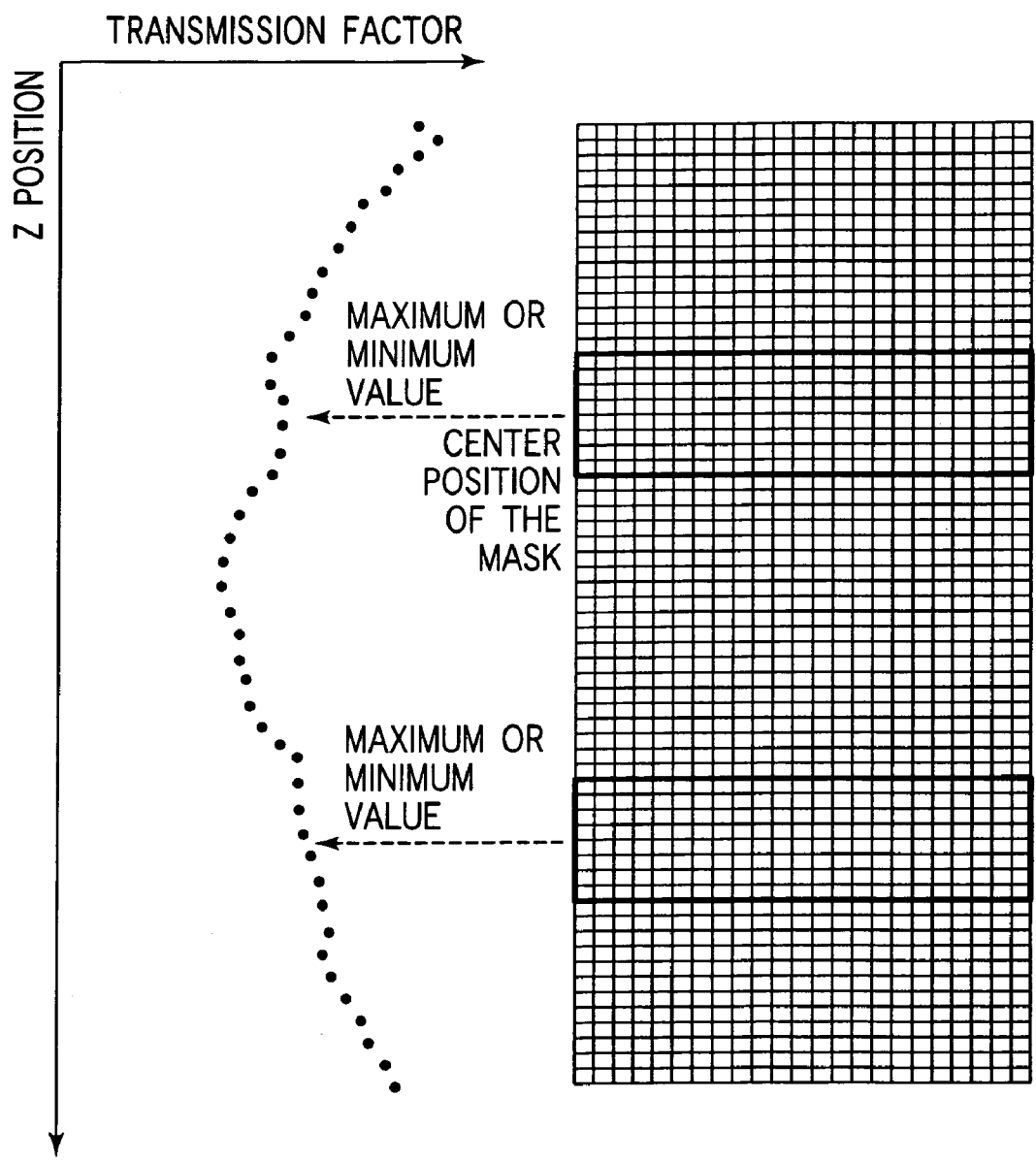

As shown in FIG. 9B, the mask is moved in the slice direction by a unit distance (S8), and the processing in steps S4 to S6 is repeated until the mask reaches the end position in step S7 (see FIG. 9C). With this operation, as shown in FIGS. 10A and 10B, the discrete distribution of X-ray transmission factors F(z) in the slice direction is generated. Note that the above unit distance is initially set to either the resolution in the slice direction of the scanogram or the width of the detection element lines 14. The unit distance can be arbitrarily changed in accordance with an instruction from the user.

A continuous distribution (to be referred to as a transmission profile) of X-ray transmission factors F(z) in the slice direction is generated from the discrete distribution of X-ray transmission factors F(z) in the slice direction by interpolation (S9). This transmission profile is stored in the data storing unit 35.

In general, the X-ray transmission factor F(z) at the shoulder or abdominal portion is lower than that at the chest portion. Since the lungs exist in the chest portion and the chest portion is mostly occupied by the air in the lungs, the X-ray transmission factor becomes high. In contrast to this, since the bones exist in the shoulder portion and the organs exist in the abdominal portion, the X-ray transmission factor becomes low.

Note that in this embodiment, a transmission factor is calculated on the basis of the average (or maximum or minimum value) of transmitted X-ray intensities in a two-dimensional area spreading in not only the channel direction but also the slice direction. This makes it possible to realize suitable tube current control in a multi-slice scan with a significantly large field of view in the slice direction as compared with a single-slice scan.

Figure 11:
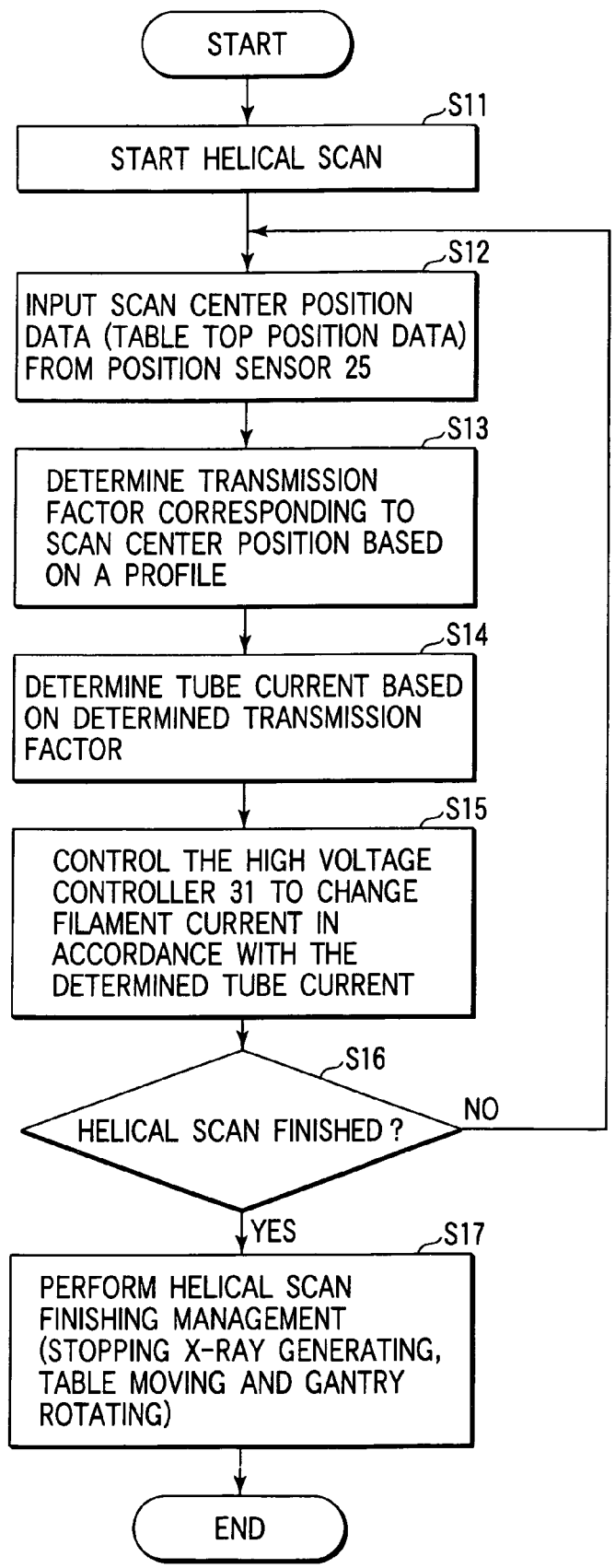
FIG. 11 is a flow chart showing the flow of tube current control (X-ray intensity control) in a helical scan by a scan controller in FIG. 3.

FIG. 11 shows a tube current control procedure using a transmission factor profile in a helical scan. A helical scan is started under the control of the scan controller 30 (S11). In the helical scan, the table top 2a is moved at a constant velocity, and the X-ray tube 10 and X-ray detector 11 are continuously rotated together. During this period, X-ray are continuously generated, and signals are read from the X-ray detector 11 at a predetermined cycle.

The position data of the table top 2a are sequentially supplied from the position sensor 25 to the scan controller 30 at a predetermined cycle (S12). For the sake of descriptive convenience, assume that the position of the table top 2a coincides with a scan center position. The scan center position is the Z position of a central axis of X-rays diverging in the slice direction (Z-axis direction) in the moving coordinate system of the table top 2a. A transmission factor read request is output to the data storing unit 35, together with position data, under the control of the system controller 44. The X-ray transmission factor data corresponding to the position is read out from the data storing unit 35 to the tube current value calculating unit 42 (S13). The tube current value calculating unit 42 calculates a tube current value on the basis of the readout X-ray transmission factor (S14).

Figure 12A:
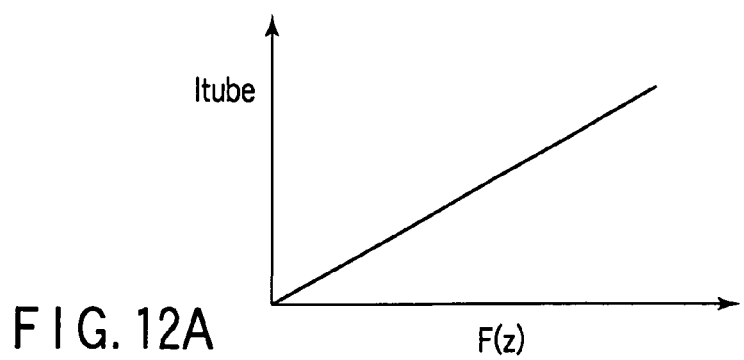
FIGS. 12A to 12D are graphs showing various relationships between X-ray transmission factors and tube currents which are stored in a data storing unit in FIG. 3.
Figure 12B:
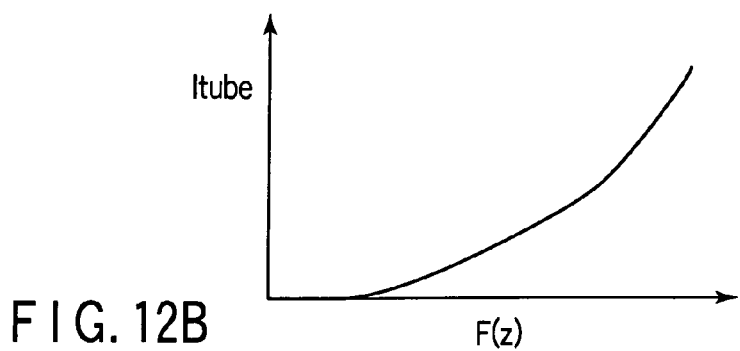

FIG. 12A is a graph showing the general relationship between the X-ray transmission factor F(z) and the tube current (Itube). As shown in FIG. 12A, the X-ray transmission factor F(z) is proportional to the tube current value (Itube). By using such a graph, a tube current (Itube) value can be uniquely specified from the X-ray transmission factor F(z). In practice, a tube current value (Itube) is calculated from the readout X-ray transmission factor F(z) in accordance with a functional expression that defines the relationship between the X-ray transmission factor F(z) and the tube current (Itube). Alternatively, the relationship between the X-ray transmission factor F(z) and the tube current (Itube) may be calculated in advance, and the calculation result may be held in the form of a table. In this case, the tube current value calculating unit 42 is formed as a ROM designed to output a tube current value (Itube) corresponding to the input X-ray transmission factor F(z).

Figure 12C:
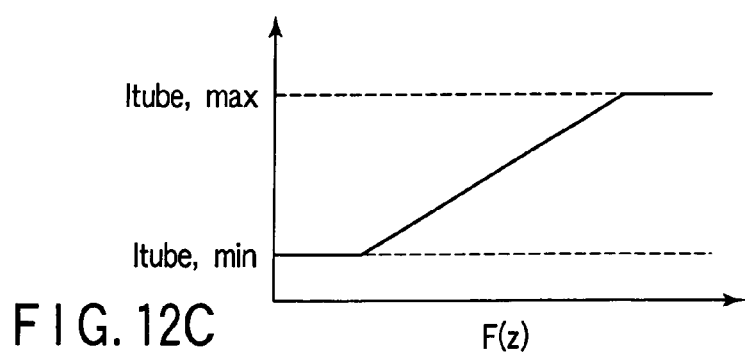
Figure 12D:
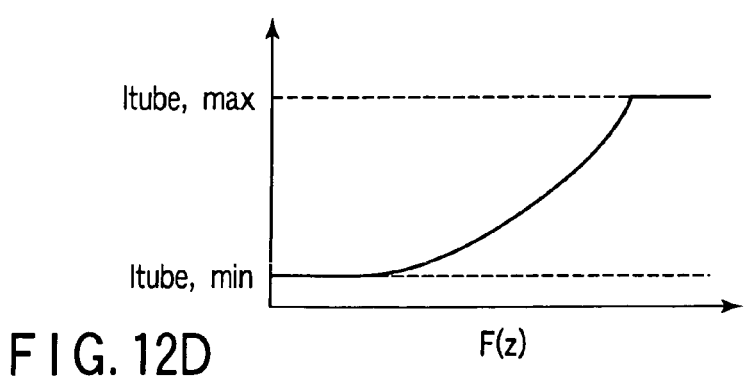

The relationship between the X-ray transmission factor F(z) and the tube current (Itube) is not limited to the proportional relationship shown in FIG. 12A. The exponential function shown in FIG. 12A may be used. In practice, X-rays are exponentially attenuated when passing through the object P, and hence using an exponential curve (Itube=expFx(z)) as the relationship between the X-ray transmission factor F(z) and the tube current (Itube) is a more practical. This therefore makes it possible to obtain a more suitable tube current value (Itube). As shown in FIGS. 12C and 12D, an upper limit (Itube, max) and lower limit (Itube, min) may be set for the tube current value (Itube). This makes it possible to always generate X-rays within the capacity range of the X-ray tube and prevent electrical discharge of the X-ray tube.

Referring back to FIG. 11, the scan controller 30 controls a filament current such that a current flows between the cathode and the anode of the X-ray tube 10 in accordance with the determined tube current value (S15). The processing in steps S12 to S15 is repeated until the helical scan is terminated in step S16. The helical scan is terminated when the table top reaches the end position of the planned scan range (S17).

Figure 13:
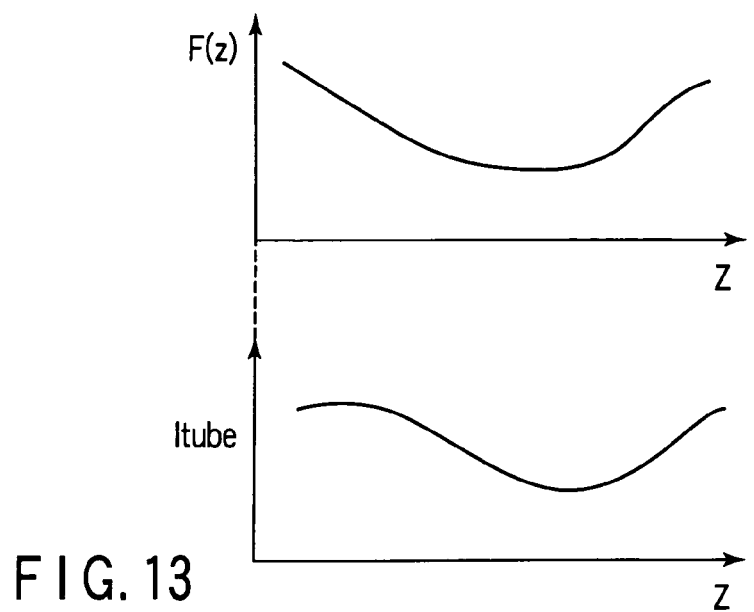
FIG. 13 is a graph showing a change in tube current over time in this embodiment.

As shown in FIG. 13, the tube current Itube is dynamically changed upon movement of the table top 2a by controlling the tube current Itube on the basis of the profile of the transmission factor F(z) in the slice direction. The transmission factor F(z) is calculated on the basis of the average (or maximum or minimum value) of transmission X-ray intensities in the two-dimensional area spreading in not only the channel direction but also the slice direction, and a tube current is controlled on the basis of the transmission factor. With this operation, suitable tube current control can be realized even in a multi-slice scan with a wide field of view in the slice direction as compared with a single-slice scan.

The difference between the effect obtained by using the average of transmitted X-ray intensities in a two-dimensional area to control a tube current (Itube) and that obtained by using the maximum value (minimum value) will be briefly described below. When the average is used, an abrupt change in the X-ray transmission factor of an object can be properly handled, and the occurrence of extremely ugly image noise, artifacts, and the like can be prevented, thus always suppressing the image noise, artifacts, and the like uniformly (with a certain range). If the maximum value (or minimum value) is used, image noise, artifacts, and the like can be suppressed more.

According to the above description, a tube current is dynamically controlled in accordance with the movement of the table top 2a in the slice direction by using one transmission factor profile corresponding to one direction. A tube current may be controlled with higher precision in accordance with not only the movement of the table top 2a in the slice direction but also a change in the rotational angel of the X-ray tube 10. For this purpose, at least two transmission factor profiles corresponding to two directions are required.

Figure 14:
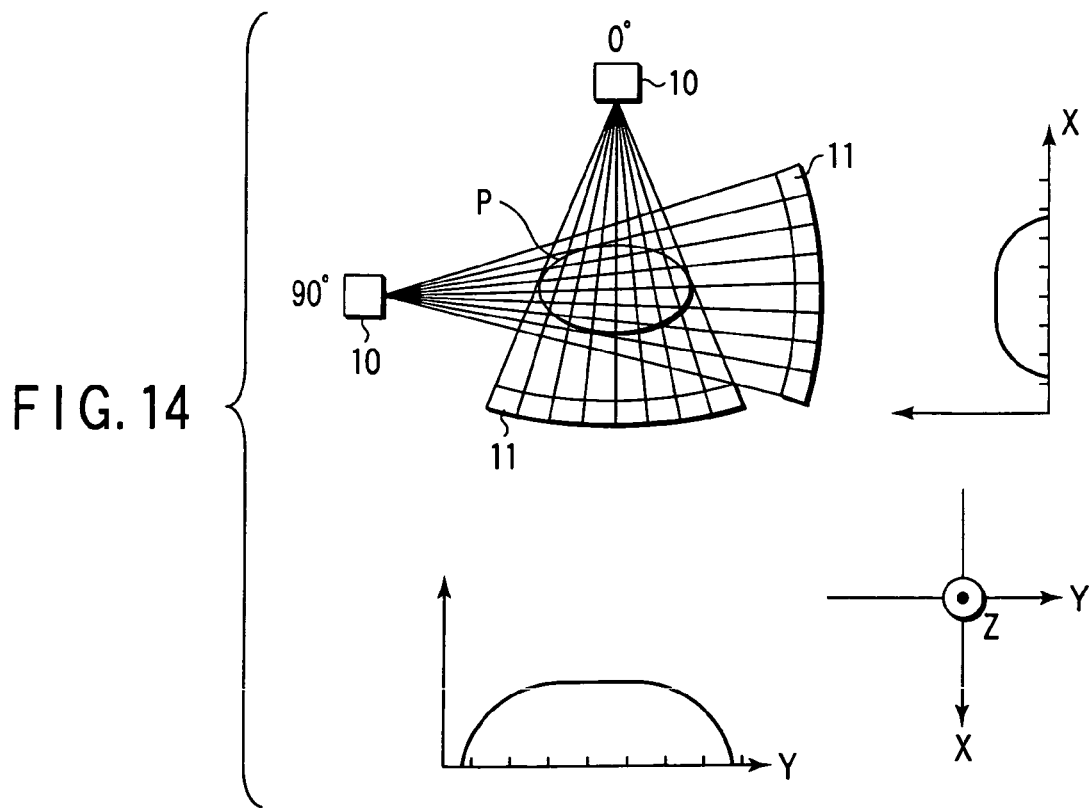
FIG. 14 is a view showing how scanogram data in two orthogonal directions are acquired in a modification to this embodiment.

As shown in FIG. 14, scanogram data are acquired while the X-ray tube 10 is fixed to an angle position of 0°. In addition, scanogram data are acquired while the X-ray tube 10 is fixed at an angle position of 90°. Scanogram data are acquired in two directions in this manner. Two transmission factor profiles Fx(z) and Fy(z) are generated on the basis of the two scanograms in different directions by the processing shown in FIG. 5. The profile Fx(z) corresponds to the 0° position of the X-ray tube 10. The profile Fy(z) corresponds to the 90° position of the X-ray tube 10. FIG. 15A shows transmission factor profiles Fx(z)ave and Fy(z)ave obtained from the averages within the mask. FIG. 15B shows transmission factor profiles Fx(z)max and Fy(z)max obtained from the maximum values within the mask. In general, the human body is flattened in the X direction, and hence Fy(z) is lower than Fx(z). The user can selectively use either of them.

The X-ray transmission factor profile Fx(z) corresponds to the 0° rotation angle of the X-ray tube 10 (almost corresponds to 180° as well). The X-ray transmission factor profile Fy(z) corresponds to the 90° rotational angle of the X-ray tube 10 (almost corresponds to 270° as well). The transmission factor profile Fx(z) represents the maximum transmission factor throughout 360°. In contrast to this, the transmission factor profile Fy(z) represents the minimum transmission factor throughout 360°. Therefore, the actual transmission factor during a helical scan changes between the two transmission factor profiles Fx(z) and Fy(z) upon rotation of the X-ray tube 10. The distance (helical pitch) the table top moves while the X-ray tube 10 makes one rotation is defined as one cycle. FIG. 15C shows a new transmission factor profile F'(z) generated such that a straight line or sine wave alternates twice between the transmission factor profiles Fx(z) and Fy(z) in each cycle.

By controlling a tube current in accordance with this transmission factor profile F'(z), the tube current can be finely changed in accordance with not only a change in transmission factor due to the movement of the table top 2a but also a change in transmission factor due to the rotation of the X-ray tube 10.

According to the above description, a transmission factor profile is obtained in advance on the basis of the scanogram data acquired before a scan, and a tube current is dynamically controlled during the scan in accordance with the transmission factor profile. However, a transmission factor may be calculated on the basis of the data acquired during a scan, and a tube current may be dynamically controlled along with the progress of a helical scan on the basis of the transmission factor.

Figure 16A:
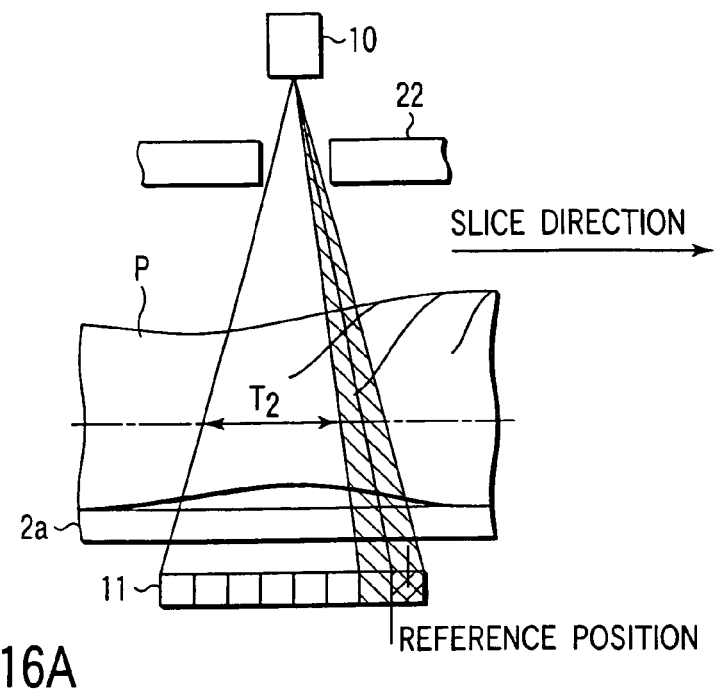
FIGS. 16A and 16B are views showing how basic data for a transmission factor are acquired during a scan in another modification to this embodiment.
Figure 16B:
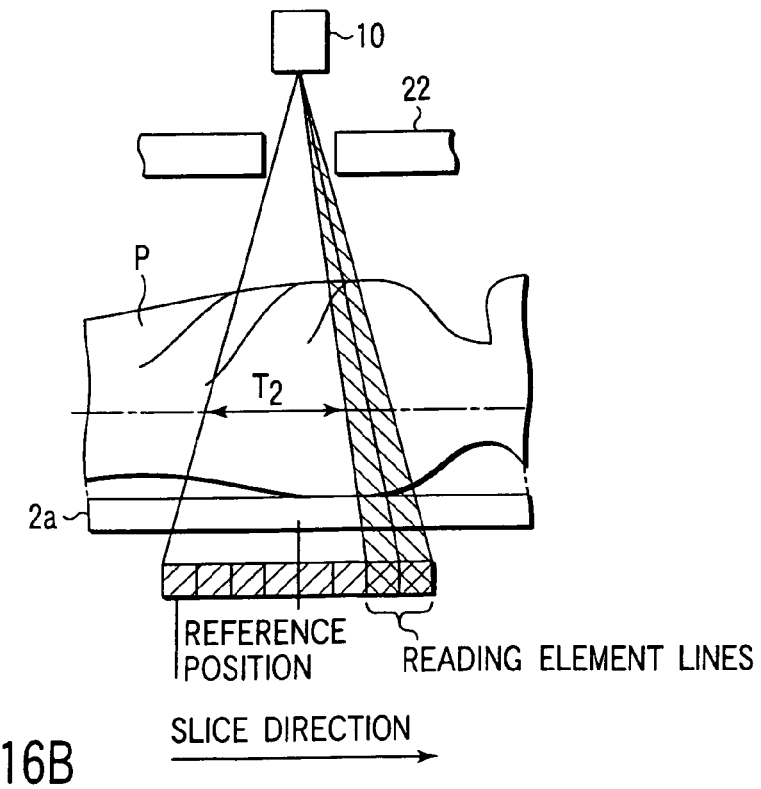

As shown in FIGS. 16A and 16B, basic data for the calculation of a transmission factor are acquired from detection element lines corresponding to a scan width T2, i.e., at least two detection element lines (oblique lines) preceding a detection element line that is set to acquire data for image reconstruction. For example, when basic data are acquired at the reference position shown in FIG. 16A and a helical scan proceeds the position shown in FIG. 16B, a tube current at the position is determined in accordance with the transmission factor calculated from the basic data acquired at the reference position shown in FIG. 16A. That is, a transmission factor is calculated from the average (or maximum or minimum value) of transmitted X-ray intensities of a plurality of channels acquired by at least two preceding detection element lines. When the center of a detection element line set to acquire data for image reconstruction reaches the position where the transmission factor data are acquired, a tube current is controlled in accordance with the transmission factor.

Figure 17A:
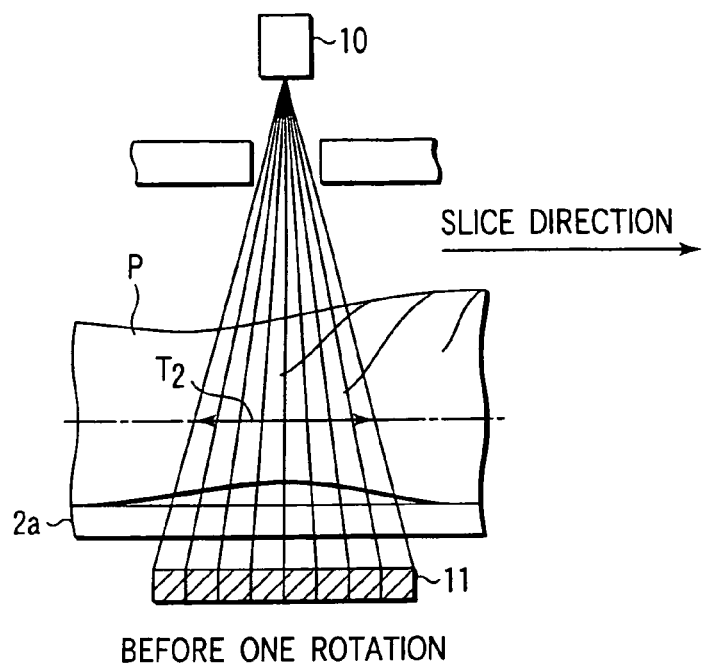
FIGS. 17A and 17B are views showing how a scan is done in still another modification to this embodiment.
Figure 17B:
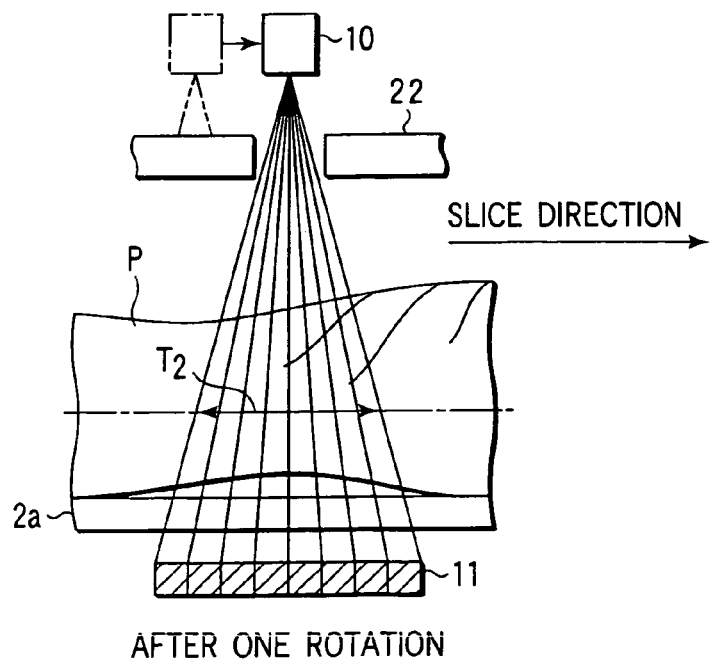

Basic data for the calculation of a transmission factor may be acquired by at least two detection element lines set to acquire data for image reconstruction before half rotation or one or a few rotations. That is, a transmission factor is calculated from the average (or maximum or minimum value) of transmitted X-ray intensities of a plurality of channels acquired by at least two detection element lines before one or a few rotations shown in FIG. 17A, and a tube current after one or a few rotations shown in FIG. 17B is dynamically controlled along with the progress of a helical scan in accordance with the transmission factor.

As described above, the same effect as that described above can be obtained by controlling a tube current in real time on the basis of the data acquired by at least two element lines immediately before rotation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus, comprising:
    an X-ray tube configured to generate X-rays with which an object to be examined is irradiated;
    a high voltage generator configured to generate a high voltage to be applied to said X-ray tube;
    an X-ray detector configured to have a plurality of X-ray detection element lines for detecting X-rays transmitted through the object;
    a scanogram generating unit configured to generate a scanogram based on an output from said X-ray detector;
    a reconstructing unit configured to reconstruct an image based on the output from said X-ray detector;
    a tube current determining unit configured to determine a tube current value for said X-ray tube, for a given slice position, based on pixel values of a plurality of pixels included in a two-dimensional partial region of the scanogram, the two-dimensional partial region being defined by slice and channel directions, wherein the partial region is different for each given slice position; and
    a control unit configured to control said high voltage generator based on the determined tube current value.

2. An apparatus according to claim 1, wherein the two-dimensional partial region has a size corresponding to the number of detection element lines corresponding to an aperture width of a collimator in the slice direction, which is placed between said X-ray tube and the object, and the number of channels constituting each of the detection element lines.

3. An apparatus according to claim 1, wherein said tube current determining unit is configured to determine a tube current value for said X-ray tube based on an average of pixel values of a plurality of pixels included in the two-dimensional partial region.

4. An apparatus according to claim 3, further comprising:
    a storing unit configured to store a table in which the tube current value is associated with the average.

5. An apparatus according to claim 1, wherein said tube current determining unit is configured to determine a tube current value for said X-ray tube based on a maximum or minimum value of pixel values of a plurality of pixels included in the two-dimensional partial region.

6. An apparatus according to claim 1, wherein said tube current determining unit is configured to determine a plurality of tube current values at a plurality of discrete positions, and said control unit dynamically changes a tube current of said X-ray tube based on the determined plurality of tube current values upon movement of the object.

7. An apparatus according to claim 6, wherein said tube current determining unit is configured to interpolate a tube current value corresponding to an intermediate position of the plurality of discrete positions from the determined tube current value.

8. An apparatus according to claim 1, wherein said reconstructing unit is configured to reconstruct the image based on outputs from at least two X-ray detection element lines selected from said plurality of X-ray detection element lines in accordance with a user instruction.

9. An apparatus according to claim 8, wherein the two-dimensional partial region has a size corresponding to the number of channels constituting each of said X-ray detection element lines and the number of selected X-ray detection element lines.

10. An apparatus according to claim 1, further comprising:
a display unit configured to display a size of the scanogram together with a frame representing the two-dimensional partial region.

11. An apparatus according to claim 10, further comprising:
an input device configured to arbitrarily change a size of the frame.

12. An apparatus according to claim 10, further comprising:
an input device configured to arbitrarily change a shape of the frame.

13. An X-ray computed tomography apparatus comprising:
an X-ray tube configured to generate X-rays with which an object to be examined is irradiated;
a high voltage generator configured to generate a high voltage to be applied to said X-ray tube;
an X-ray detector configured to have a plurality of X-ray detection element lines for detecting X-rays transmitted through the object;
a reconstructing unit configured to reconstruct an image on the basis of outputs from at least two X-ray detection element lines selected in accordance with a slice thickness and the number of slices indicated by a user instruction;
a tube current determining unit configured to determine a tube current value for said X-ray tube, for a given slice position, on the basis of an output distribution, X-ray transmission factor distribution, or X-ray attenuation factor distribution of said X-ray detector which corresponds to a range corresponding to the slice thickness and the number of slices, wherein the range is different for each given slice position; and
a control unit configured to control said high voltage generator on the basis of the determined tube current value,
wherein said range corresponds to at least two slice positions.

14. An X-ray computed tomography apparatus, comprising:
an X-ray tube configured to generate X-rays with which an object to be examined is irradiated;
a high voltage generator configured to generate a high voltage to be applied to said X-ray tube;
an X-ray detector configured to have a plurality of X-ray detection element lines for detecting X-rays transmitted through the object;
a reconstructing unit configured to reconstruct an image based on the output from said X-ray detector; and
a control unit configured to dynamically control said high voltage generator for a given slice position based on a profile of the object in a slice direction which is associated with an X-ray transmission index, wherein said profile includes at least two slice positions and the at least two slice positions are different for each given slice position.

15. An apparatus according to claim 14, wherein said control unit is configured to dynamically control said high voltage generator based on an average in a predetermined interval of the profile.

16. An apparatus according to claim 15, wherein the predetermined interval has a size corresponding to the number of detection element lines corresponding to an aperture width of a collimator in a slice direction which is placed between said X-ray tube and the object.

17. An apparatus according to claim 15, further comprising:
an input device configured to input a length of the interval.

18. An apparatus according to claim 15, wherein a length of the interval is determined on the basis of the number of X-ray detection lines, which is not less than two, selected from the plurality of X-ray detection element lines to reconstruct the image in accordance with a user instruction.

19. An X-ray computed tomography apparatus, comprising:
an X-ray tube configured to generate X-rays with which an object to be examined is irradiated;
a high voltage generator configured to generate a high voltage to be applied to said X-ray tube;
an X-ray detector configured to have a plurality of X-ray detection element lines for detecting X-rays transmitted through the object;
a moving mechanism configured to move the object relative to said X-ray tube and said X-ray detector;
a reconstructing unit configured to reconstruct an image based on outputs from at least two detection element lines selected from said plurality of X-ray detection element lines in accordance with a user instruction; and
a control unit configured to dynamically control a tube current value for said X-ray tube, for a given slice position, along with relative movement of the object based on outputs from at least two of said at least two selected detection element lines, wherein said at least two selected detection element lines are arranged in a slice direction and are different for each given slice position.

20. An apparatus according to claim 19, wherein said control unit is configured to control a tube current value for said X-ray tube based on an output from at least one start line of said at least two selected detection element lines.

21. An apparatus according to claim 19, wherein said control unit is configured to determine a tube current value for said X-ray tube based on an average of outputs from at least some of said at least two selected detection element lines.

22. An apparatus according to claim 19, wherein said control unit is configured to determine a tube current value for said X-ray tube based on a maximum or minimum value of outputs from at least some of said at least two selected detection element lines.

23. An X-ray computed tomography apparatus, comprising:
an X-ray source configured to generate X-rays with which an object to be examined is irradiated;
an X-ray detector configured to have a plurality of X-ray detection element lines for detecting X-rays transmitted through the object in a body axis direction of the object;

a scanographic control unit configured to cause scanography of the object to be done by using said X-ray source and said X-ray detector;

a scanogram generating unit configured to generate a scanogram based on X-ray data obtained by the scanography;

a display unit configured to display the scanogram;

a setting unit configured to set a slice thickness and the number of slices by using said display unit;

a tube current determining unit configured to determine a tube current value for the X-ray source for a given slice position in a scan based on X-ray data obtained by scanography corresponding to a scan range which is simultaneously scanned with the slice thickness and the number of slices, wherein the scan range corresponds to at least two slice positions and is different for each given slice position; and a scan control unit configured to cause a scan to be done in the scan range with the tube current value determined by said tube current value determining unit.

24. An X-ray computed tomography apparatus, comprising:

an X-ray source configured to generate X-rays with which an object to be examined is irradiated;

a collimator configured to be placed between said X-ray source and the object to collimate the X-rays in a body axis direction of the object;

an X-ray detector configured to have a plurality of X-ray detection element lines for detecting X-rays transmitted through the object in a body axis direction of the object;

a scanographic control unit configured to cause scanography of the object to be done by using said X-ray source and said X-ray detector;

a scanogram generating unit configured to generate a scanogram based on X-ray data obtained by the scanography;

a display unit configured to display the scanogram;

a setting unit configured to set a scan condition through said display unit;

an aperture width determining unit configured to determine an aperture width of said collimator in a scan in accordance with the scan condition; and a tube current value determining unit configured to determine a tube current value for the X-ray source for a given slice position in the scan based on the X-ray data in a slice direction in a range scanned with the aperture width, wherein said range corresponds to at least two slice positions and the range is different for each given slice position.

25. An X-ray computed tomography method, comprising:

performing scanography of an object to be examined;

generating a scanogram based on X-ray data obtained by the scanography;

displaying the generated scanogram;

setting a number of slices and a slice thickness by using the scanogram;

determining a tube current value for an X-ray source for a given slice position in a scan based on the X-ray data in a slice direction corresponding to a scan range scanned with the number of slices and the slice thickness, wherein the scan range corresponds to at least two slice positions and the scan range is different for each given slice position; and scanning the scan range with the determined tube current value.

* * * * *